US008840656B2

(12) United States Patent
Costello

(10) Patent No.: US 8,840,656 B2
(45) Date of Patent: Sep. 23, 2014

(54) SPRING CONTROLLED STENT DELIVERY SYSTEM

(75) Inventor: Kieran Costello, Ballina-Killaloe (IE)

(73) Assignee: Cook Medical Technologies LLC, Bloomington, IN (US)

( * ) Notice: Subject to any disclaimer, the term of this patent is extended or adjusted under 35 U.S.C. 154(b) by 159 days.

(21) Appl. No.: 13/529,016

(22) Filed: Jun. 21, 2012

(65) Prior Publication Data

US 2013/0006346 A1 Jan. 3, 2013

Related U.S. Application Data

(60) Provisional application No. 61/502,988, filed on Jun. 30, 2011.

(51) Int. Cl.
*A61F 2/06* (2013.01)
*A61F 2/966* (2013.01)
*A61F 2/95* (2013.01)

(52) U.S. Cl.
CPC ......... *A61F 2/966* (2013.01); *A61F 2002/9522* (2013.01); *A61F 2002/9511* (2013.01); *A61F 2002/9665* (2013.01)
USPC ...................................................... 623/1.11

(58) Field of Classification Search
CPC ..... A61F 2/95; A61F 2002/9505; A61F 2/97; A61F 2/954; A61F 2/958; A61F 2/962; A61F 2/966; A61F 2002/9511; A61F 2002/9517; A61F 2002/9522; A61F 2002/9534; A61F 2002/9583; A61F 2002/9586; A61F 2002/9665
USPC ........ 606/1.11, 1.12, 1.2, 108, 200; 623/1.11, 623/1.12, 1.2
See application file for complete search history.

(56) References Cited

U.S. PATENT DOCUMENTS

| | | | | |
|---|---|---|---|---|
| 4,913,141 A | * | 4/1990 | Hillstead .................... | 623/1.11 |
| 5,443,477 A | * | 8/1995 | Marin et al. ................ | 606/198 |
| 5,562,698 A | * | 10/1996 | Parker ........................ | 606/200 |
| 5,571,135 A | * | 11/1996 | Fraser et al. ............... | 623/1.12 |
| 5,591,195 A | * | 1/1997 | Taheri et al. ............... | 623/1.11 |

(Continued)

FOREIGN PATENT DOCUMENTS

WO    WO 2005/037361 A2    4/2005

OTHER PUBLICATIONS

International Search Report mailed Oct. 15, 2012 for International Application No. PCT/US2012/043435.

(Continued)

*Primary Examiner* — Melanie Tyson
*Assistant Examiner* — Christian Knauss
(74) *Attorney, Agent, or Firm* — Brinks Gilson & Lione

(57) ABSTRACT

A stent delivery system and a method for releasably constraining a stent and a method of implanting a stent are provided. The stent delivery system includes an elongate shaft including a proximal portion, a distal portion, a lumen extending at least partially therethrough, and a stent receiving portion on the distal portion of the shaft. The stent delivery system also includes a stent positioned at the stent receiving portion of the elongate shaft, the stent having a constrained configuration and an expanded configuration. A first biasing member is operably connected to the shaft and the stent and a second biasing member is operably connected to the shaft and the stent. The first and second biasing members have a first configuration cooperatively applying a longitudinal tensioning force to the stent and a second configuration cooperatively releasing the longitudinal tensioning force on the stent.

13 Claims, 8 Drawing Sheets

(56) References Cited

U.S. PATENT DOCUMENTS

| | | | |
|---|---|---|---|
| 6,168,616 B1 * | 1/2001 | Brown, III | 623/1.11 |
| 6,572,643 B1 * | 6/2003 | Gharibadeh | 623/1.11 |
| 2003/0028235 A1 | 2/2003 | McIntosh et al. | |
| 2004/0147939 A1 * | 7/2004 | Rabkin et al. | 606/108 |
| 2006/0271093 A1 * | 11/2006 | Holman et al. | 606/194 |
| 2008/0039863 A1 * | 2/2008 | Keegan et al. | 606/108 |
| 2009/0287290 A1 * | 11/2009 | Macaulay et al. | 623/1.11 |
| 2010/0082089 A1 * | 4/2010 | Quadri et al. | 623/1.11 |
| 2011/0071613 A1 * | 3/2011 | Wood et al. | 623/1.11 |

OTHER PUBLICATIONS

Written Opinion of the International Searching Authority mailed Oct. 15, 2012 for International Application No. PCT/US2012/043435.

* cited by examiner

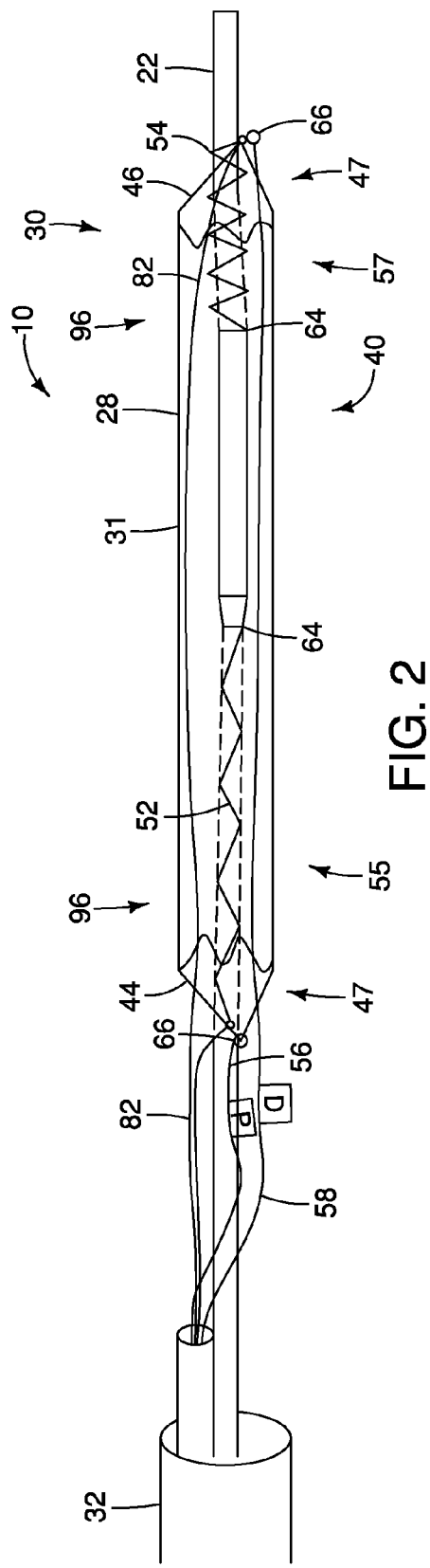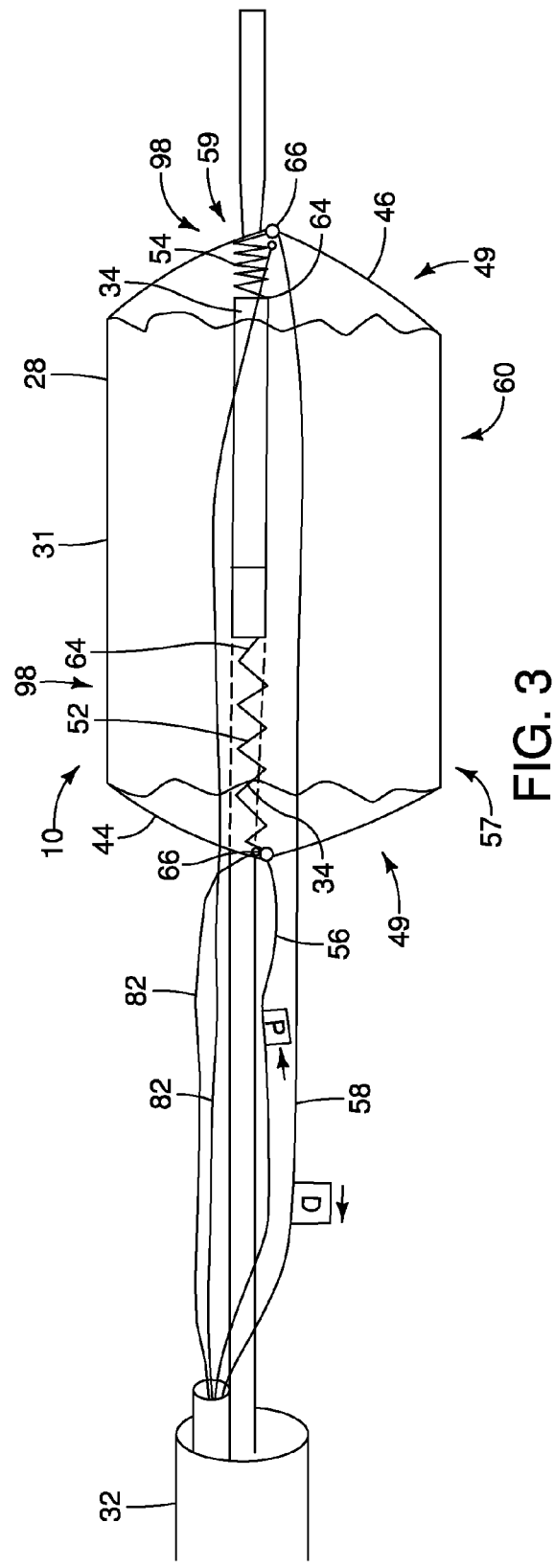

SPRING CONTROLLED STENT DELIVERY SYSTEM

RELATED APPLICATIONS

This application claims the benefit of U.S. Provisional Application No. 61/502,988, filed Jun. 30, 2011, which is incorporated by reference herein in its entirety.

TECHNICAL FIELD

This invention relates to a medical device and, in particular to a device for delivering and deploying a stent and a method of delivering and deploying the stent into a body lumen.

BACKGROUND

A self-expanding stent is typically introduced into the body using a delivery device that includes an outer sheath coaxially disposed and slidable over an inner catheter. The stent is disposed at the distal end of the device between the inner catheter and the outer sheath and held in a compressed position by the outer sheath. The inner catheter and the outer sheath move coaxially with respect to each other. The stent may be deployed by proximally pulling back the outer sheath relative to the inner catheter until the stent is exposed. The self-expanding stent expands from the stent distal end to the stent proximal end as the sheath is proximally withdrawn.

Several problems may occur with the sheathed delivery device described above. The delivery devices using a sheath to hold the stent in position may be difficult to reposition or remove and slow to operate. For example, in order to maintain the ability to remove or reposition the stent before final release of the stent into the patient, the stent may only be partially deployed by proximally withdrawing the sheath. Once the stent is fully deployed, i.e. radially expanded with the sheath fully withdrawn, the sheath cannot reconstrain the stent. Difficulties may arise utilizing a conventional outer sheath/inner catheter delivery device that may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded into the body lumen. Additionally, retraction of the outer sheath with controlled movement may not be possible because the physician is manually retracting the outer sheath which may lead to uneven or inadvertent jerking back of the outer sheath that can lead to improper positioning of the stent.

Additionally, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the distal end of the stent is positioned first while the proximal portion of the stent is still covered by the outer sheath. Accurate placement of the proximal portion of the stent and/or the stent body may be important in certain applications, for example to prevent stent migration or to properly open a stricture along the entire length of the stricture. An additional drawback occurs with the sheathed stent delivery system where direct visualization of the stent is required. For example, in endoscopically placed stents, the sheath tends to prevent or obscure the location of the stent, making accurate placement of the stent more difficult.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catheters and hysteresis in the movement of the stent.

Accordingly, in view of the potential drawbacks of current technology, there is a desire for a delivery system that can increase the control, accuracy and ease of placement of a stent during deployment of the stent within a patient and allow for expansion of the stent centrally, distally, proximally and/or towards a central reference position. The delivery system would ideally reduce the risk of malfunction while providing for a smoother, more accurate and quicker deployment of the entire stent. The delivery system also would provide the ability to reconstrain, recapture, reposition and/or remove the stent after expansion of the stent. The delivery system may also include a marker system viewable to the operator for accurate placement of the stent.

SUMMARY OF THE INVENTION

Accordingly, it is an object of the present invention to provide a device and a method having features that resolve or improve on one or more of the above-described drawbacks.

The foregoing object is obtained in one aspect of the present invention by providing a stent delivery system. The stent delivery system includes an elongate shaft including a proximal portion, a distal portion, a lumen extending at least partially therethrough, and a stent receiving portion on the distal portion of the shaft. The stent delivery system also includes a stent positioned at the stent receiving portion of the elongate shaft, the stent having a constrained configuration and an expanded configuration. A first biasing member is operably connected to the shaft and the stent and a second biasing member is operably connected to the shaft and the stent. The first and second biasing members have a first configuration cooperatively applying a longitudinal tensioning force to the stent and a second configuration cooperatively releasing the longitudinal tensioning force on the stent.

In another aspect of the present invention, a method for releasably constraining a stent in a delivery system is provided. The method includes positioning a stent on an elongate shaft, engaging a first portion of the stent with a first biasing member and engaging a second portion of the stent with a second biasing member. The method further includes moving a pull wire operably connected to at least one of the first and the second biasing members and biasing at least one of the first and second biasing members to place longitudinal tension on the stent to constrain the stent against the elongate shaft.

In another aspect of the present invention, a method for implanting a stent using a stent delivery system is provided. The method includes inserting a distal portion of a stent delivery system into the lumen of a patient. The stent delivery system includes an elongate shaft including a proximal portion, a distal portion, a lumen extending at least partially therethrough, and a stent receiving portion on the distal portion of the shaft. The stent delivery system also includes a stent positioned at the stent receiving portion of the elongate shaft, the stent having a constrained configuration and an expanded configuration. A first biasing member is operably connected to the shaft and the stent and a second biasing member is operably connected to the shaft and the stent. The method further includes holding the stent in the constrained configuration with longitudinal tensile force applied to the stent by the first and second biasing members in a first position and tensioning the stent for delivery of the stent to the implant site, positioning the stent at the implant site, expanding the stent to the expanded configuration by moving the first and second members to a second position and releasing longitudinal force on the stent.

BRIEF DESCRIPTION OF THE DRAWINGS

FIG. 2 is a partial view of the distal portion of the system shown in FIG. 1 showing the stent in a constrained configuration;

FIG. 3 is a side view of the system shown in FIG. 2 with the stent in a expanded configuration;

DETAILED DESCRIPTION OF THE EMBODIMENTS

Figure 1:
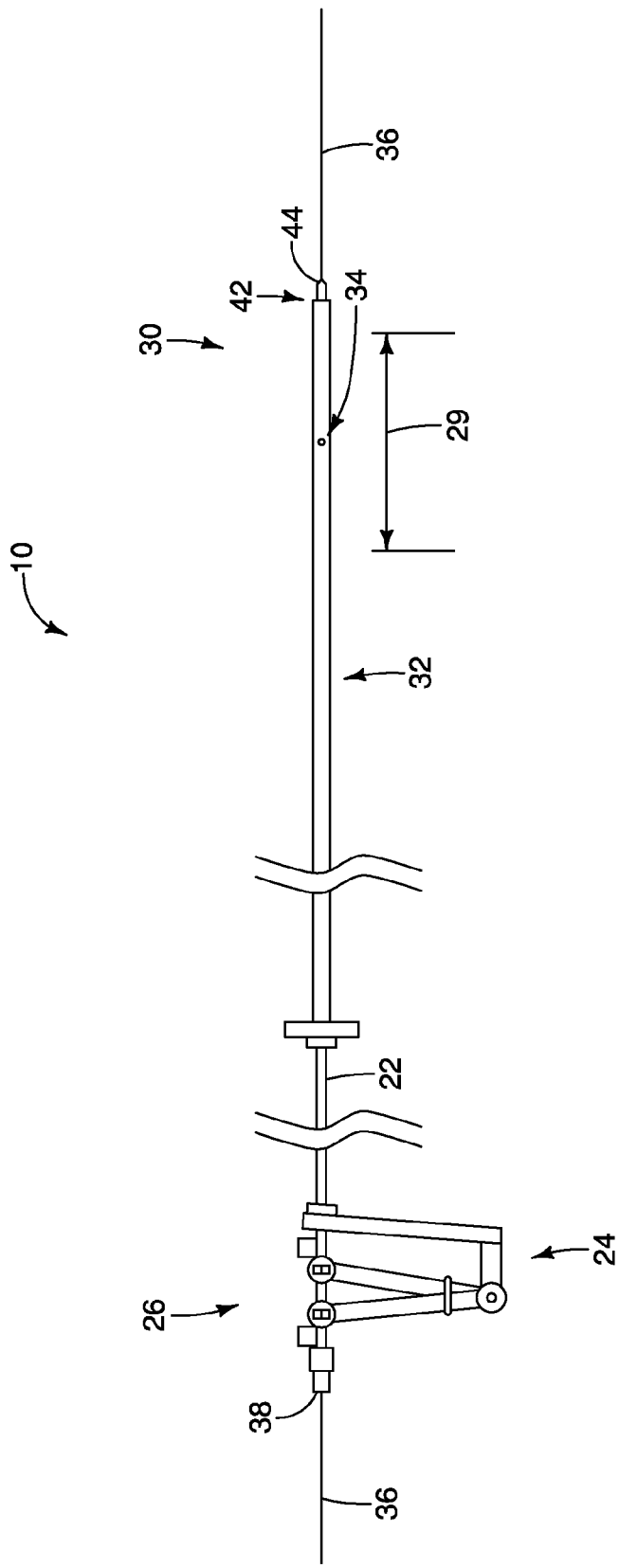
FIG. 1 is a side view of a stent delivery system according to an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the delivery system that is farthest from the physician and the term "proximal" means the portion of the delivery system that is nearest to the physician.

FIG. 1 illustrates a stent delivery system 10 in accordance with embodiments of the present invention. The delivery system 10 is shown in FIG. 1 and includes an inner shaft 22 and a handle 24 at a proximal portion 26 of the system 10. A stent 28 (shown in FIG. 2) is positionable on a stent region 29 of the inner shaft 22 at a distal portion 30 of the delivery system 10. The stent delivery system 10 may optionally include an outer sheath 32 slidably positionable over a portion of the inner shaft 22 to cover the stent region 29 and the stent 28. One or more radiopaque markers 34 may be included on the delivery system 10 to indicate the position of the stent 28. The stent delivery system 10 may also include a guidewire 36 extendable through a port 38 of the inner shaft 22 through a distal tip 41 at the distal portion 30 of the delivery system 10. The optional outer sheath 32 is shown in FIG. 1 extended distally over the stent 28 and abutting the distal tip 41 of the inner shaft 22 forming a smooth outer surface 42 of the delivery system 10. The outer sheath 32 is operably connected to the handle 24. The outer sheath 32 may be provided to facilitate a smoother delivery of the system 10 through a bodily lumen of the patient. The outer sheath 32 may be releasably locked against the handle 24 to keep the sheath 32 stationary relative to the handle 24. In some embodiments, the outer sheath 32 is provided with a rapid exchange port. In embodiments, provided without the outer sheath 32, the stent 28 is held collapsed closely against the inner shaft 22 for delivery to the patient site.

FIG. 2 illustrates a partial view of the distal portion 30 of the stent delivery system 10 shown in FIG. 1. As shown in FIG. 2, the stent 28 is in a constrained configuration 40 collapsed against the inner shaft 22. In some embodiments, the stent 28 may be a self-expanding stent. The stent 28 may be any kind of stent that has a tendency to radially collapse when a longitudinal force is applied to the ends of the stent. By way of non-limiting example, the stent 28 may be formed as a woven mesh formed from a metal or polymer or a laser cut pattern formed in a metal stent. The stent may also be formed from a bioabsorbable material. One example of a woven stent is the EVOLUTION® stent (Wilson-Cook Medical, Inc.)

As shown in FIG. 2, the sheath 32 has been proximally withdrawn and the stent 28 exposed in a constrained configuration 40. The stent 28 is held in the constrained configuration 40 by a mechanism that may be provided with or without the outer sheath 32, an embodiment of which is described in detail below with reference to FIGS. 6-8, that includes a proximal stent constraining member 44 connected to a first biasing member 52 and a distal stent constraining member 46 connected to a second biasing member 54 to longitudinally provide tension on the stent 28 to constrain the stent 28 and hold the stent 28 collapsed against the inner shaft 22 as shown in FIG. 2. The proximal and distal constraining members 44, 46 are connected to the stent 28 in a first position 47 shown in FIG. 2. The stent delivery system 10 further includes a first pull wire 56 operably connected to the first biasing member 52 and a second pull wire 58 operably connected to the second biasing member 54. The pull wires 56, 58 are provided to move the biasing members 52, 54 longitudinally along the inner shaft. The pull wires 56, 58 may be any type of mechanism for providing movement of the biasing members 52, 54 and are not limited to wires. The pull wires 56, 58 may be operably connected to the handle 24 to control the movement of the pull wires 56, 58 and the biasing members 52, 54.

The first and second biasing members 52, 54 are movable between expanded and relaxed configurations to place the stent 28 under longitudinal tension and to release the longitudinal tension. The biasing members 52, 54 may be provided as a spring, such as a coil spring or a flat spring. The springs may be tension, extension, torsion or compression springs. Any type of biasing member known to one skilled in the art may be used in the delivery system 10 that provides a tensioning force on the stent 28 that may be relaxed. The first pull wire 56 is operably connected to the first biasing member 52 to move the biasing member 52 between an extended configuration 55 and a relaxed configuration 57 as shown in FIGS. 2 and 3, respectively. The second pull wire 58 is operably connected to the second biasing member 54 to move the second biasing member 54 between the relaxed configuration 57 and a compressed configuration 59 as shown in FIGS. 2 and 3, respectively. Other combinations of extended, relaxed and compressed configurations for the biasing members are also possible. The relationships between the biasing members 52, 54 shown in FIGS. 2 and 3 are for illustrative purposes and are meant to be non-limiting. The biasing members 52, 54 may be configured so that a central portion 31 of the stent 28 remains in the same position as the stent 28 is moved between the constrained configuration 40 and the expanded configuration 60.

The stent 28 is shown in an expanded configuration 60 in FIG. 3 where the stent 28 is expanded away from the inner shaft 22. The proximal and distal constraining members 44, 46 are in a second position 49 and remain connected to the stent 28 but the longitudinal tensioning force on the stent 28 has been removed to allow the stent 28 to expand away from the inner shaft 22. The first and/or second biasing members 52, 54 are expanded or contracted as will be explained below to release the tension on the proximal and distal constraining members 44, 46 to allow the stent 28 to expand to the expanded configuration 60. In some embodiments, one of the first or the second biasing member 52, 54 may remain stationary and the other of the first or the second biasing member 52, 54 is expanded, relaxed or compressed to expand the stent 28 to the expanded configuration 60. The first and/or second biasing members 52, 54 may be expanded, relaxed or compressed to return the stent to the constrained configuration shown in FIG. 2. With the proximal and distal constraining members 44, 46 connected to the stent 28, the stent 28 may be repeatedly fully expanded and contracted for proper positioning of the stent 28 at a treatment position or for removal by moving the first and/or second biasing members 52, 54 between extended, relaxed and compressed positions, 55, 57, 59.

Figure 4:
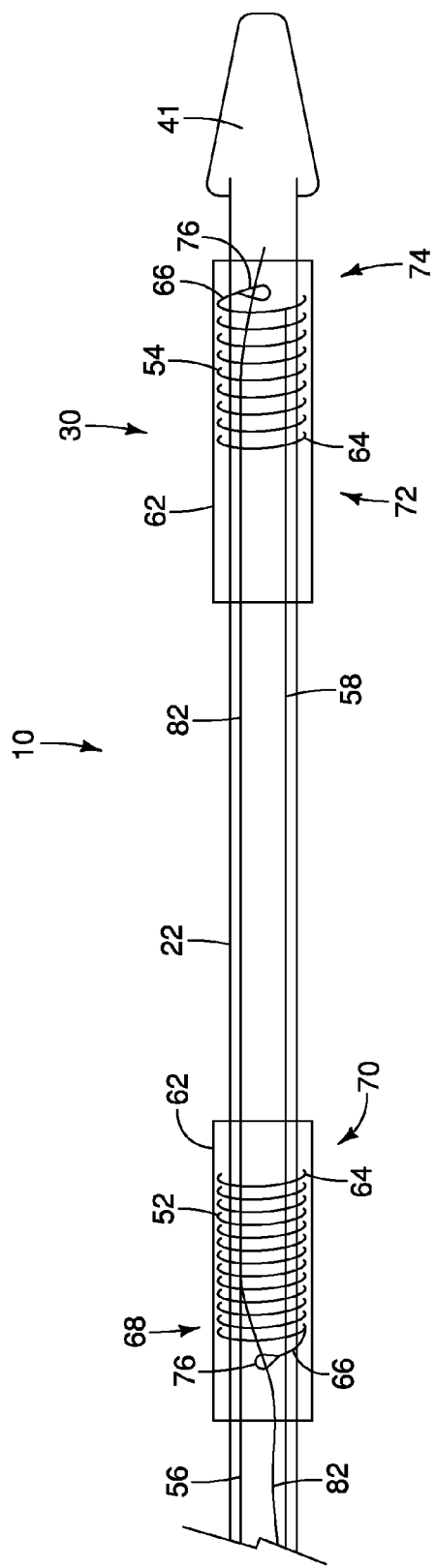
FIG. 4 is a side view of the distal portion of an embodiment of a stent delivery system shown without the stent.

The distal portion 30 of the stent delivery device 10 is shown in FIG. 4 without the stent 28 for clarity. The first and second biasing members 52, 54 are sized to move freely on the inner catheter 22. Optionally, one or more tubular covers 62 may be provided over the biasing members 52, 54 to protect the stent 28 from the biasing members 52, 54. In some embodiments, a single cover 62 may be provided to cover both the first and second biasing members 52, 54. Each of the first and second biasing members 52, 54 includes a fixed end portion 64 fixed to the inner shaft 22 and a free end portion 66 movable in relation to the inner shaft 22. The fixed and free ends 64, 66 of the first and second biasing members 52, 54 may be provided in opposite orientations. As shown in FIG. 4, by way of non-limiting example, the first biasing member 52 may include the free end portion 66 at a proximal end 68 of the first biasing member 52 and the fixed end portion 64 at a distal end 70 of the first biasing member 52. The second biasing member 54 may include the fixed end portion 64 at a proximal end 72 of the second biasing member 54 and the free end portion 66 at a distal end 74 of the second biasing member 54. Alternatively, the fixed and free end portions 64, 66 of the first and second biasing members 52, 54 may be provided in the same orientation relative to the shaft 22 or in the opposite orientation to the orientation shown in FIG. 4.

The free end portions 66 may each include a loop 76. One or more retaining wires 82 may be inserted through the loops 76 and connected to the first and second constraining members 44, 46 as described below to secure the stent 28 to the delivery system 10. A single retaining wire 82 is shown through both loops 76 in FIG. 4. See FIG. 2 showing proximal and distal retaining wires 82. (Discussed in more detail below.) FIG. 4 illustrates the first pull wire 56 connected to the free end portion 66 of the first biasing member 52 and the second pull wire 58 connected to the free end portion 66 of the second biasing member 54. The first and second biasing members 52, 54 have a stiffness constant (k) that is greater than the stiffness constant of the stent 28. The greater stiffness constant of the first and second biasing members 52, 54 allows the stent 28 to be actuated by the biasing members 52, 54 rather than the biasing members 52, 54 being actuated by the stent 28. The first biasing member 52 and the second biasing member 54 may have the same or different stiffness constants. In some embodiments, the first and second biasing members 52, 54 are provided as springs.

Figure 5:
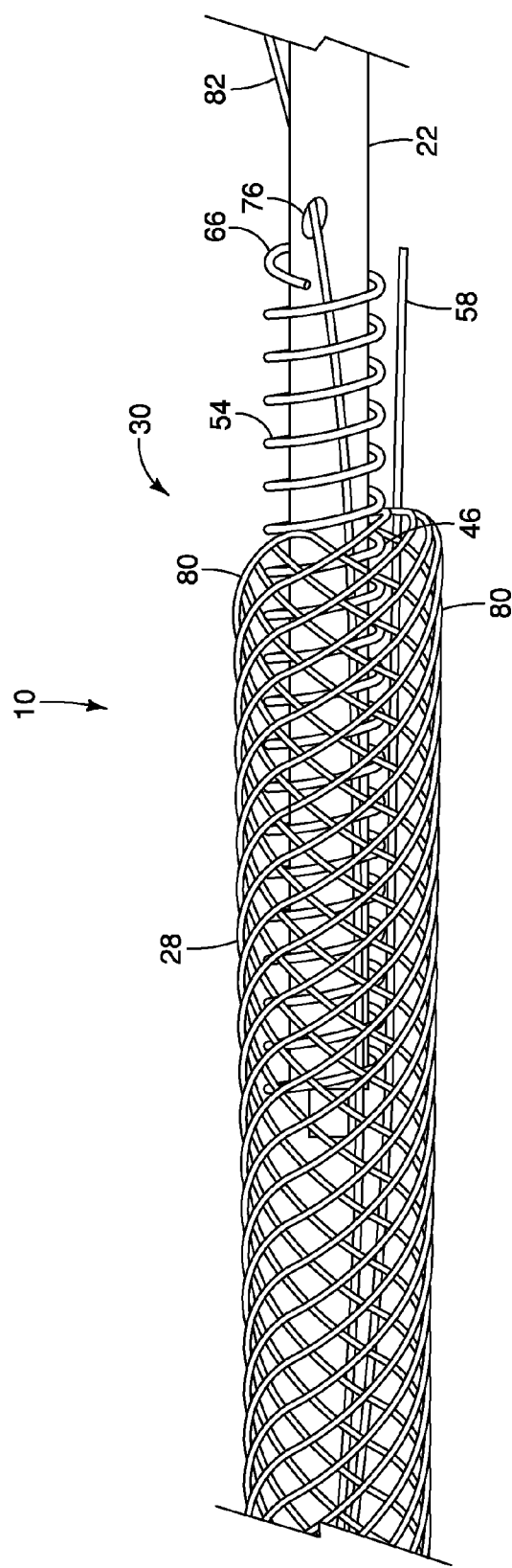
FIG. 5 is an enlarged view of the distal portion of the system shown in FIG. 2.

FIG. 5 illustrates the distal portion 30 of the stent delivery system 10 with the stent 28 positioned on the inner shaft 22 over a portion of the second biasing member 54. The distal constraining member 46 is looped through a plurality of crowns 80 of the stent 28. The retaining wire 82 is shown connected to the distal constraining member 46 and through the loop 76 on the free end portion 66 of the second biasing member 54. The retaining wire 82 holds the distal constraining member 46 and the stent 28 to the second biasing member 54 connected to the inner shaft 22 in both the expanded configuration 60 and the compressed configuration 40. When the stent 28 is in the proper position at the treatment site, the retaining wire 82 may be withdrawn, for example by proximally withdrawing the retaining wire 82, to release the distal constraining member 46 from connection to the inner shaft 22. Similarly, the proximal constraining member 44 may be released by withdrawing with the same retaining wire 82 that holds the distal constraining member 46 or a separate retaining wire 82 may be provided and withdrawn to release the proximal constraining member 44. The retaining wire 82 is withdrawn from the loop 76 on the free end portion 66 of the first biasing member 52 so that the connection between the proximal constraining member 44, the loop 76 and the retaining wire 82 is removed.

Figure 6:
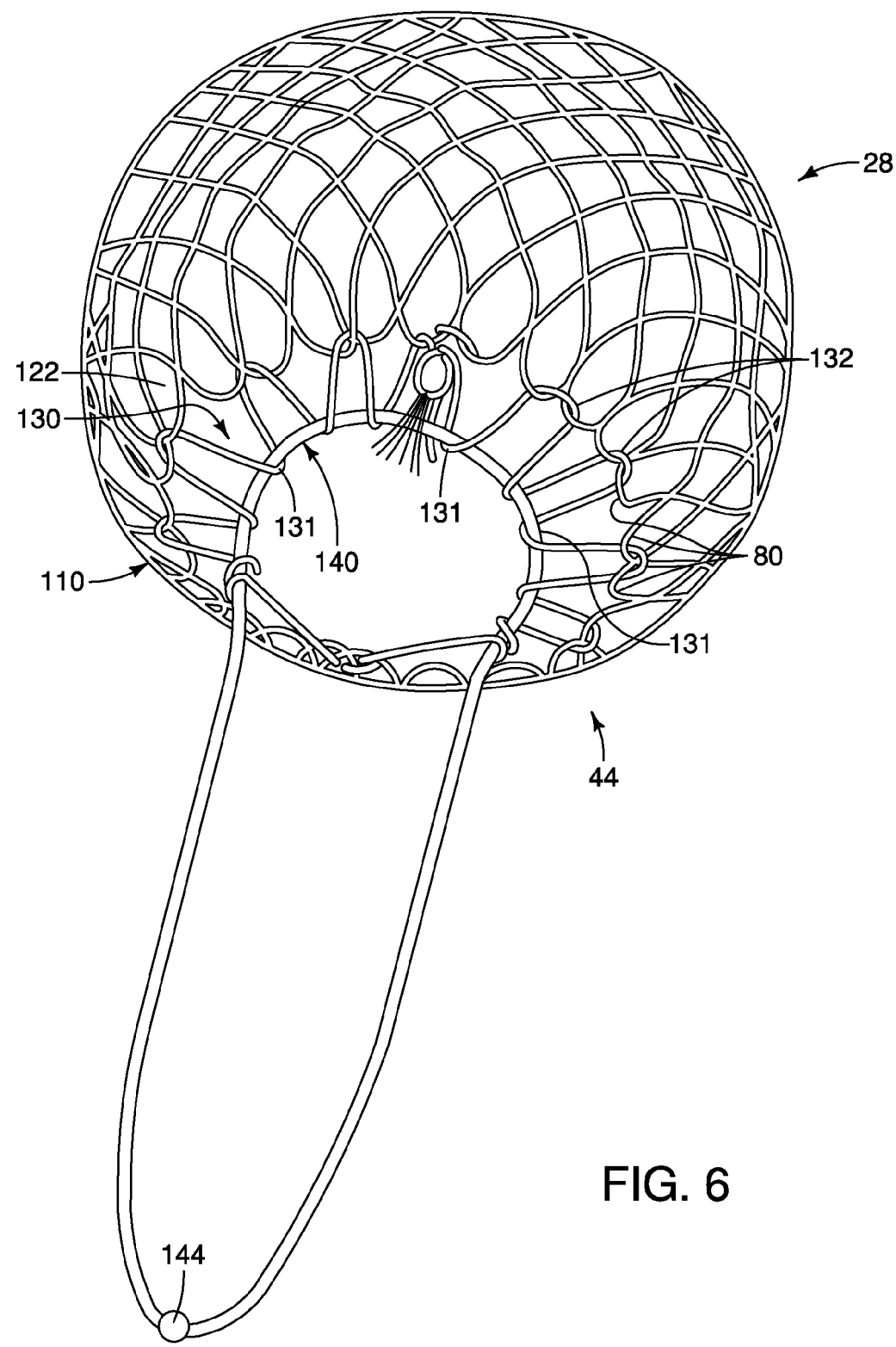
FIG. 6 is an enlarged view of the stent shown in FIG. 2, illustrating a constraining member is a partial side view of a distal portion of the stent and the device shown in FIG. 4 illustrating a distal constraining member.
Figure 7:
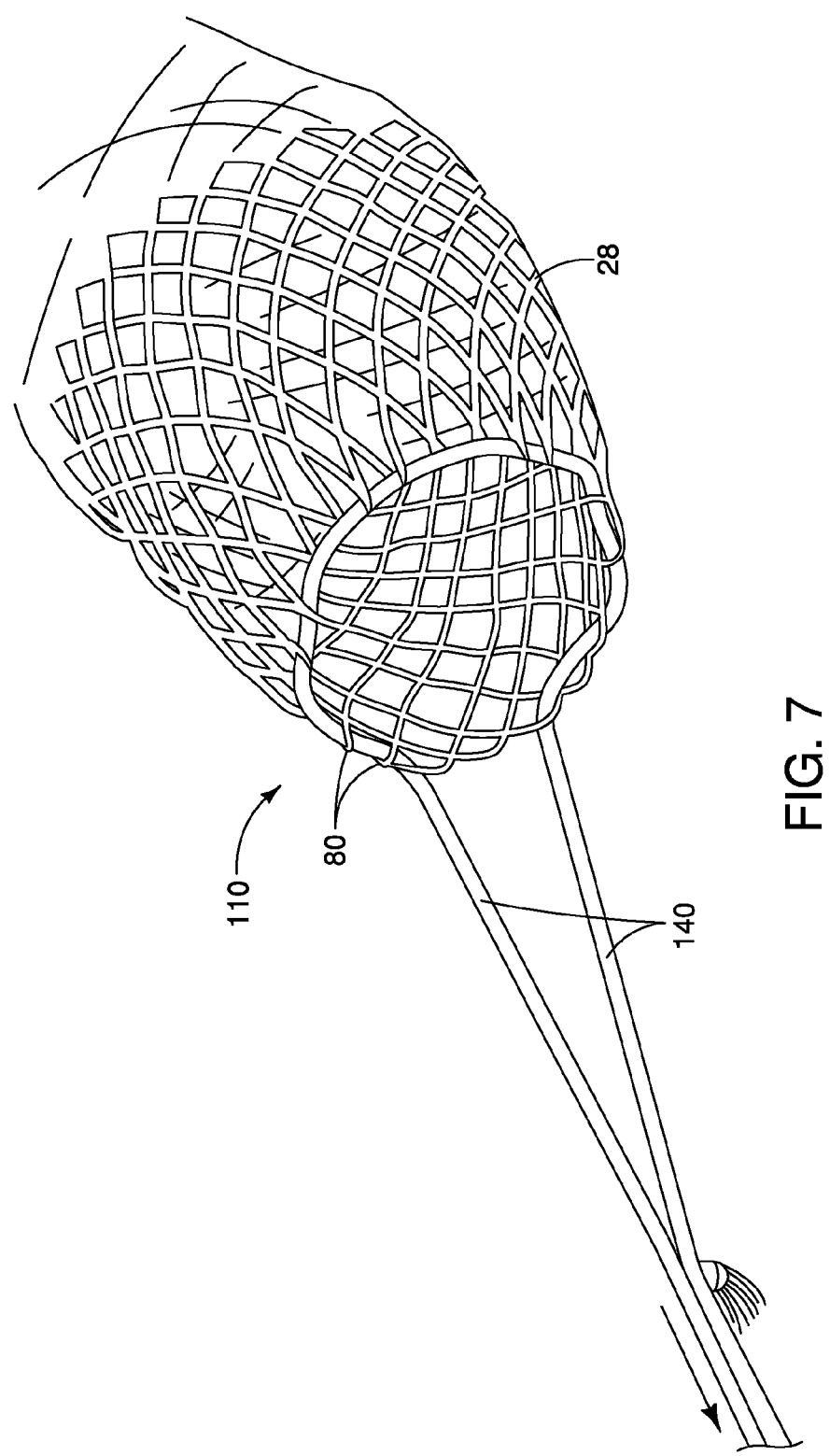
FIG. 7 is an enlarged view of an alternative embodiment of a constraining member.

An exemplary embodiment of the proximal constraining member 44 is illustrated in FIG. 6 and is connected to the first biasing member 52 (See FIG. 2). The distal constraining member 46 is not shown but is similarly configured to the proximal constraining member 44 and is connected to the second biasing member 54 (See FIG. 2). As shown in FIG. 6, the proximal constraining member 44 includes an outer filament 130 and an inner filament 140. Loops 132 of the outer filament 130 may be interwoven through one or more peaks 80 at an end portion 110 of the stent 28. The inner filament 140 engages with loops 131 of the outer filament 130 to pull the outer filament 130 taught and to reduce the diameter of the stent end portion 110 and close the end portion 110 and the stent body against the inner shaft 22 in response to movement of the first biasing member 52. The inner filament 140 includes an end portion 144 that is configured to cooperate with the retaining wire 82 to releasably lock the inner filament 140 to the first biasing member 52 on the inner shaft 22 to allow selective expansion and contraction of the stent 28 as described above.

The retaining wire 82 may be connected to the handle 24 for proximal withdrawal of the retaining wire 82 from the loops 76 of the first and second biasing members 52, 54 and the end portions 144 of the inner filament 140 of the proximal and distal constraining members 44, 46 to completely release the stent 28 from the delivery system 10. The withdrawal of the retaining wires 82 may be simultaneous or sequential when two retaining wires 82 are present. Because the stent 28 has been expanded and positioned in the proper position within the lumen of the patient, the timing of the release of the retaining wires 82 is not critical for the positioning of the stent 28.

While the proximal and distal restraining members 44, 46 have been described with reference to connection to the end portions 110 of the stent 28, it is also possible to provide proximal and distal constraining members 44, 46 that are connected to other portions of the stent 28 and still provide a constrained configuration 40 for the stent 28. For example, the proximal constraining member may be connected to a mid proximal portion or mid-point of the stent and the distal constraining member may be connected to the distal end portion of the stent. Similarly, the proximal constraining member may be connected to the proximal end portion of the stent and the distal constraining member may be connected to the midpoint of mid distal portion of the stent or both the proximal and distal constraining members may be connected to other than the proximal and distal end portions of the stent. In some embodiments, the proximal or the distal constraining members or both proximal and distal constraining members may be connected to the stent at a plurality of positions on the stent.

In some embodiments, the stent delivery system 10 may be provided with proximal and distal constraining members 44, 46 having the outer filament 140 woven through the peaks 80 at the end portion 110 of the stent 28 without including an inner filament. The outer filament 140 is shown woven though the peaks 80 of the stent 28 in FIG. 7. The outer filament 140 may be connected to the first and second biasing members 52, 54 and cooperatively connected to the inner shaft 22 by the retaining wire(s) 82 as described above with reference to FIG. 6.

Figure 8:
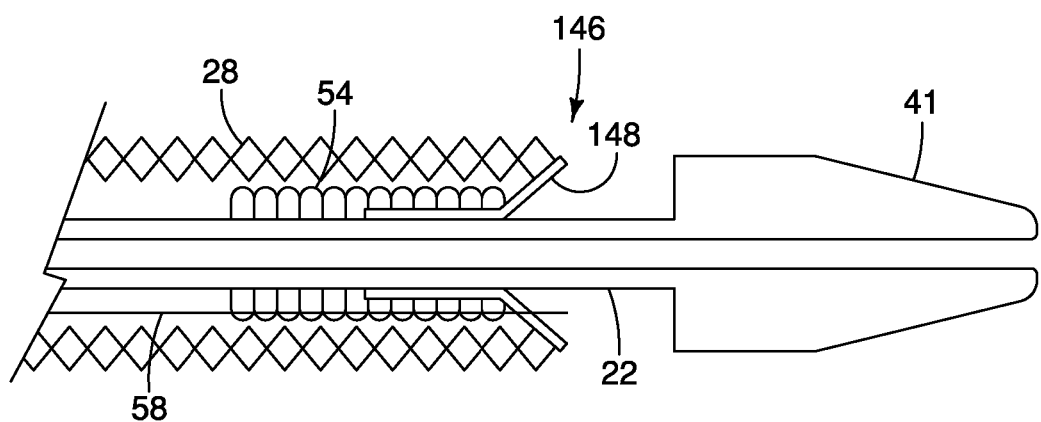
FIG. 8 is a partial side view of an alternative embodiment of a distal constraining member.

Additional configurations for the proximal and distal constraining members are also possible. By way of non-limiting example, an additional configuration for an alternative embodiment of the constraining members is shown in FIG. 8 illustrating a distal constraining member 146. A similar proximal constraining member is also provided, but not shown. The proximal and distal constraining members may be the same or different for the stent delivery system. FIG. 8 illustrates alternative embodiment of a distal constraining member 146 that includes one or more hooks 148 that may hook onto peaks 80 of the stent 28. The hooks 148 also connect to and are movable with the second biasing member 54 in response to movement of the second pull wire 58. The stent 28 is movable in response to expansion or contraction of the biasing member 54 to constrain the stent 28 on the inner shaft 22 or to expand the stent 28.

A plurality of hooks 148 may be provided connected to the biasing member 54 and spaced apart to evenly hold the stent 28 in position. For example, 4 hooks may be provided and spaced apart by 90°. Other combinations of numbers of hooks and spacing of the hooks may also be provided, including asymmetric spacing and uneven numbers of hooks. One or more hooks 148 may be provided with a retaining wire 188 (not shown) extending through the hook 148 and the stent peak 80 to releasably lock the stent 28 to the delivery system 10, for example, similar to the embodiment described above with reference to FIG. 6. The hook 148 may be released from the stent peak 80 by withdrawing the retaining wire 82 and releasing the lock between the peak 80 and the hook 148, for example. The stent 28 may be expanded and constrained a plurality of times prior to release of the retaining wire 188 similar to the embodiments described above.

Additional constraining members may also be used with the stent delivery system 10 that connect the stent to the first and second biasing members. The constraining members describe above are meant to be exemplary and non-limiting.

Figure 9:
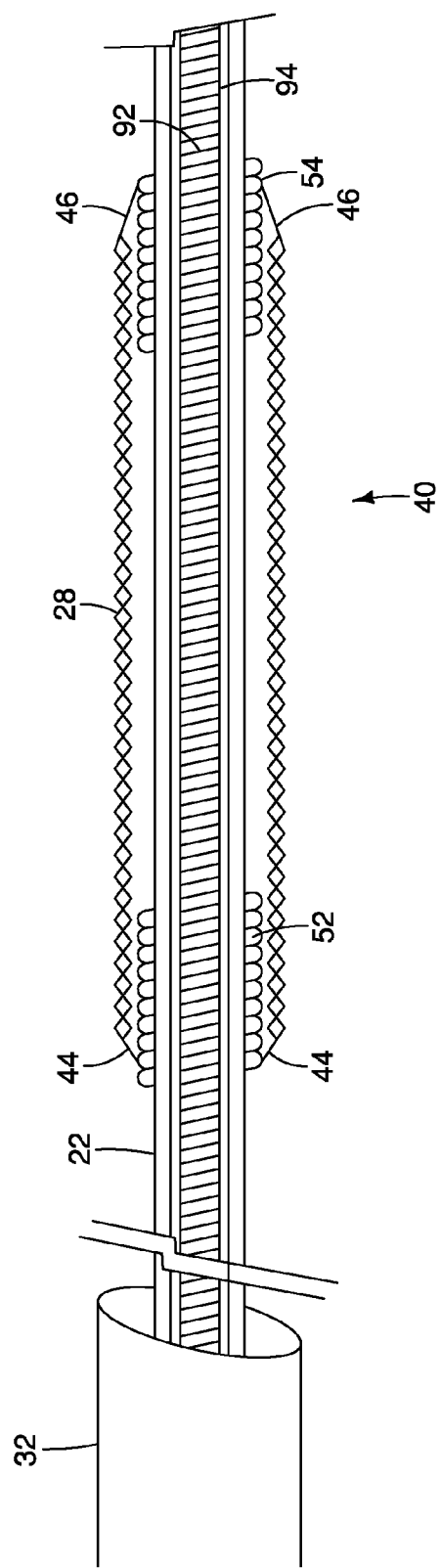
FIG. 9 is a sectional view of a delivery system illustrating a stiffening member.

In some embodiments, a stiffening member 92 may be removably provided in a lumen 94 of the inner shaft 22 as shown in FIG. 9. The stiffening member may be provided as a mandrel, catheter, rod and the like that is removably insertable into the lumen 94. The stiffening member 92 may be provided to help increase the rigidity of the inner shaft 22 against the inward tensioning force of the stent 28 when the stent 28 is in the constrained configuration 40. In some embodiments, the inner shaft 22 may be provided in a soft material to facilitate passage through the body lumen. In the event that the materials are sufficiently soft, the inner shaft 22 may collapse or deform in response to the tensioning force of the stent 28 provided by the first and second constraining members 44, 46 being biased by the first and second biasing members 52, 54 longitudinally constraining the stent 28 against the inner shaft 22.

The stiffening member 92 may be made from any material having suitable stiffness to provide support for the inner shaft 22 with the stent 28 longitudinally tensioned on the inner shaft 22. Exemplary materials for forming the shaft include, but are not limited to, metal alloys such as stainless steel, tantalum or its alloys, tungsten, platinum, gold, copper, palladium, rhodium, nickel, or a superelastic alloys, such as nitinol or polymers that can be provided with sufficient shore hardness, such as Pebax, Peek, polyimide, liquid crystal polymers (LCP) such as Vectran, polyethylene, polyethylene terephthalate and Nylon.

The outer sheath 32 may be provided for delivery of the stent to the area of the treatment site and then proximally withdrawn before positioning the stent 28. The outer sheath 32 may be used to compress the stent 28 against the inner shaft 22 for delivery of the device 10 to the treatment site with the stiffening member 92 removed and the stent 28 in the constrained configuration 40. (See FIG. 1.) The stiffening member 92 may be inserted into the lumen 94 when the stent 28 is near the proper position for implantation into the patient and the outer sheath 32 is over the stent 28. The outer sheath 32 may be withdrawn and the stent 28 remains constrained on the inner shaft 22 by the proximal and distal constraining members 44, 46. The stiffening member 92 supports the inner shaft 22 against the compressive tensioning force exerted by first and second biasing members 52, 54.

The materials used to manufacture the components of the stent delivery systems described herein may be any materials known to one skilled in the art that are suitable for use in patients. By way of non-limiting example, the shafts and sheaths may be formed from polytetrafluorothylene (PTFE) particularly when a low friction outer sheath is desirable. Nylon and HDPE may also be used for clarity. Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon including multi-layer or single layer structures and the like and may also include reinforcement wires, braid wires, coils, coil springs and or filaments. The stent may be formed from but is not limited to the following materials: Nickel titanium alloys, for example, nitinol, stainless steel, cobalt alloys and titanium alloys. In some embodiments, the stent may be formed from a polymer. The loops of the constraining members may be made from common suture material as known in the art, for example polyester suture such as 4-0 Tevdek®, nylon, silk, polypropylene, ultra high molecular weight polyethylene (UHMPE) and the like. The sutures may be monofilament, braided, twisted or multifilament. The loops, biasing members and the retaining wires may also be made from a metallic alloy such as stainless steel or nickel titanium. In some embodiments, the stent, the loops and/or the retaining wires may be made from biodegradable materials. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; expoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, collagen.

Other suitable biocompatible materials may also be used for any of the components described herein.

Operation of the stent delivery systems of the present invention is described with reference to the stent delivery system 10 by way of non-limiting example. Alternative methods of operating the system may also be used. The stent delivery system 10 may be provided in a sterile packaging. The stent 28 may be provided in the expanded configuration 60 or constrained configuration 40 within the packaging. For example, some stent materials may weaken or otherwise deform when stored in a constrained configuration 40 with the longitudinal tension exerting force on the stent during shipping and storage. In some embodiments provided with an outer sheath 32, the outer sheath 32 may be provided to hold the stent 28 in position on the stent region 30 without having the first and second biasing members 52, 54 tensioning the stent 28. For example, the system 10 may be provided with the biasing members 52, 54 in a relaxed configuration 98 (see FIG. 3, for example) with the free ends portions 66 of the first and second biasing members 52, 54 positioned closer together (compare to FIG. 2) and the outer sheath 32 over the stent 28 on the inner shaft 22.

Prior to insertion of the distal portion 30 of the system 10 into the patient, the operator may move the handle 24 to add longitudinal tension to the stent 28 by moving the biasing members 52, 54 to a tensioning configuration 96 (see FIG. 2, for example) where the free end portions 66 of the first and second biasing members 52, 54 are moved further apart from each other and placing longitudinal tension on the stent 28 using the proximal and distal constraining members 44, 46 to constrain the stent 28 against the inner shaft 22. The stent 28 may be provided in the expanded configuration 60 in the absence of a sheath as well and be moved to the constrained configuration 40 by operation of the handle 24 to move the first and second biasing members 52, 54 to the biasing configuration 96 prior to delivery to the patient.

Operation of the stent delivery system 10 to constrain and expand the stent 28 will be described with reference to FIGS. 2 and 3. As will be understood by one skilled in the art, different configurations of the biasing members may also be used and the configuration shown in FIGS. 2 and 3 is by way of non-limiting example.

Minimal fluoroscopy may be used for placement of the stent 28 within the patient's lumen because the inner shaft 22 does not move to release the stent 28 and markers 34 can be placed on the inner shaft 22 for reference for the position of the stent 28 within the stricture. In some embodiments, the first and second biasing members 52, 54 may be equally and oppositely expanded and contracted for simultaneous release of the stent from the constrained configuration. The simultaneous release of the stent 28 means that the midpoint 31 of the stent 28 in the constrained configuration 40 on the inner shaft 22 is the midpoint 31 when the stent 28 is released also so that the stent 28 can be precisely positioned based on the known midpoint 31 of the stent 28. Markers may also be placed on the free end portions 66 of the biasing members 52, 54 to show the movement of the stent 28 from the constrained configuration 40 to the expanded configuration 60.

The endoscope is positioned within the lumen so the operator can view the proximal side of the stricture. The guidewire 36 is inserted through the stricture and the endoscope is removed. The proper length stent 28 is selected based on the stricture measurement. The operator inserts the distal portion 30 of the stent delivery system into the patient's lumen with the stent 28 in the constrained configuration 40 on the inner shaft 22. The guidewire 36 may be inserted first to navigate a tortuous pathway to the treatment site and the system 10 is delivered over the guidewire 36 to the treatment site. The endoscope may then be placed into the patient's lumen adjacent and parallel to the system 10. Alternatively, the stent delivery system 10 may be inserted into the patient's lumen through the working channel of an endoscope, depending on the size and location of the lumen.

A viewing port of the endoscope is used to identify the proximal end of the stricture at the treatment site. The stent 28 is positioned within the lumen at the treatment point. For embodiments having a softer inner shaft 22, the stiffening member 92 is inserted through the lumen 94 of the inner shaft 22 to provide support for the longitudinally tensioned stent. The outer sheath 32, if present, is proximally withdrawn and the stent 28 in the constrained configuration 40 is exposed within the patient's lumen. The constrained stent 28 may be moved within the lumen to correctly position the stent 28 at the treatment site. The stent 28 is moved to the expanded configuration 60 by movement of the handle 24 that moves the first and second biasing members 52, 54 so that the free end portions 66 are closer to each other and the proximal and distal constraining members 44, 46 are moved to the second position 49 releasing the longitudinal tension on the stent 28.

For example, in the tensioning configuration 96 shown in FIG. 2, the first biasing member 52 is in the extended configuration 55 with the first pull wire 56 pulling the free end portion 66 of the first biasing member proximally. The second biasing member 54 is in the relaxed configuration 57 and the second pull wire 58 is not exerting force on the second biasing member 54. To move the stent 28 from the constrained configuration 40 to the expanded configuration 60, first pull wire 56 is moved distally to move the free end portion 66 of the first biasing member 52 toward the distal end portion 30 of the inner shaft 22. The first biasing member 52 is moved to the relaxed configuration 57 to release the tension on the proximal constraining member 44. The second pull wire 58 is pulled proximally to move the second biasing member 54 to the compressed configuration 59 so that the free end portion 66 of the second biasing member 54 is moved proximally and closer to the free end portion 66 of the first biasing member 52. The tension on the distal constraining member 46 is also released and the stent 28 is expanded to the expanded configuration 60. The stent 28 may be returned to the constrained configuration 40 by the operator moving the first and second pull wires 56, 58 in the opposite directions as described above for expansion of the stent 28. Operation of the first and second pull wires 56, 58 may be simultaneous so that expansion and constraining of the stent is in equal and opposite directions.

The stent 28 may be moved from the constrained configuration 40 to the expanded configuration 60 as many times as needed.

Once the proper position for the stent 28 is achieved within the patient's lumen, the retaining wires 82 may be proximally withdrawn from connection to the stent 28, the loops 76 of the first and second biasing members 52, 54 and the proximal and distal constraining members 44, 46 to completely release the stent 28 from the proximal and distal constraining members 44, 46. The delivery system 10 is withdrawn proximally from the patient and the endoscope removed.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A stent delivery system comprising:
    an elongate shaft including a proximal portion, a distal portion, a lumen extending at least partially therethrough, and a stent receiving portion on the distal portion of the elongate shaft;
    a stent positioned at the stent receiving portion of the elongate shaft, the stent having a constrained configuration and an expanded configuration;
    a first biasing member operably connected to the elongate shaft and the stent;
    a second biasing member operably connected to the elongate shaft and the stent,
    a first pull wire operably connected to the first biasing member and configured to move the stent between the constrained and expanded configurations; and
  a second pull wire operably connected to the second biasing member;
    wherein the first and second biasing members have a first configuration cooperatively applying a longitudinal tensioning force to the stent and a second configuration cooperatively releasing the longitudinal tensioning force on the stent and wherein the second pull wire is configured to cooperate with the first pull wire to move the stent between the constrained and expanded configurations.

2. The stent delivery system of claim 1, further comprising a proximal constraining member releasably connected to a proximal portion of the stent and having a first position and a second position.

3. The stent delivery system of claim 2, wherein the proximal constraining member comprises a first filament or a hook.

4. The stent delivery system of claim 2, wherein the proximal constraining member comprises a first filament and a second filament.

5. The stent delivery system of claim 2, further comprising a distal constraining member releasably connected to a distal portion of the stent and having a first position and a second position;
    wherein the stent is in the constrained configuration with the proximal and distal constraining members in the first position.

6. The stent delivery system of claim 1, wherein the first biasing member comprises an extended configuration and a relaxed configuration.

7. The stent delivery system of claim 1, wherein the second biasing member comprises a relaxed configuration and a compressed configuration.

8. The stent delivery system of claim 1, wherein the first biasing member comprises a fixed end portion connected to the elongate shaft and a free end portion, the free end portion positioned proximal to the fixed end portion.

9. The stent delivery system of claim 1, wherein the second biasing member comprises a fixed end portion connected to the elongate shaft and a free end portion, the free end portion positioned distal to the fixed end portion.

10. The stent delivery system of claim 1, further comprising a cover covering at least one of the first and the second biasing members.

11. The stent delivery system of claim 1, further comprising a retaining wire operably connected to the stent for releasably locking the stent to the elongate shaft.

12. The stent delivery system of claim 11, wherein the retaining wire is removable from connection with the stent to completely release the stent from the elongate shaft.

13. The stent delivery system of claim 1, wherein the stent is repeatedly movable between the constrained configuration and the expanded configuration.

* * * * *